United States Patent [19]

Daeninckx et al.

[11] 4,119,578

[45] Oct. 10, 1978

[54] HYDROSOLUBLE BAR FOR USE IN TOILET BOWLS AND METHOD OF MAKING SAME WHICH INCLUDES AN EXTRUSION STEP

[75] Inventors: Jean Daeninckx, Paris; Bernard Chesbeuf, Saint Maur, both of France

[73] Assignee: L'Oreal, Paris, France

[21] Appl. No.: 682,465

[22] Filed: May 3, 1976

[30] Foreign Application Priority Data

May 2, 1975 [FR] France ................. 75 13815

[51] Int. Cl.$^2$ .................. C11D 1/14; C11D 3/24; C11D 3/32
[52] U.S. Cl. ................... 252/548; 252/174; 252/550; 252/554; 252/DIG. 16
[58] Field of Search ............... 21/55, 58; 4/222, 231, 4/228; 210/58, 59, 64; 134/42; 252/90, 548, 550, 535, 554, 174; 424/20, 76, 128, 167, 353

[56] References Cited

U.S. PATENT DOCUMENTS 2,403,613  7/1940  Reynolds .................... 252/554

FOREIGN PATENT DOCUMENTS 2,407,947  9/1974  Fed. Rep. of Germany.
774,407  5/1957  United Kingdom.

Primary Examiner—P.E. Willis, Jr.
Attorney, Agent, or Firm—Briseboise & Kruger

[57] ABSTRACT

A constituent designed to improve its extrudability is added to a composition adapted to be formed into a bar for cleaning and deodorizing a toilet bowl when suspended therein. The composition is then extruded and the resulting extrusion divided into bars. The preferred extrusion additive is a paraffin sulfonate consisting of sulfonated alkyl chains having 14 to 16 carbon atoms and having a high monosulfate content.

7 Claims, No Drawings

HYDROSOLUBLE BAR FOR USE IN TOILET BOWLS AND METHOD OF MAKING SAME WHICH INCLUDES AN EXTRUSION STEP

SUMMARY OF THE INVENTION

In order to deodorize and clean toilet bowls it is conventional to utilize water-soluble products in solid form and, in particular, in the form of a bar, which is placed inside the bowls in a position such that it is eroded by the water during flushing. The water-soluble bar progressively dissolves when brought in contact with the water and releases a small quantity of product at each flushing operation until it has been completely used up, so as to insure the cleaning and deodorization of the bowl in which it is located.

The composition of these water soluble products is variable but the basic constituent which is found in almost all of them is paradichlorobenzene because of its efficacity and its low cost. This constituent, when used in sufficient quantity in the water soluble bar, makes it possible to combat odors and reduce the development of bacteria. Moreover, it has the substantial advantage of subliming slowly and carrying perfumes contained in the bar.

To manufacture these water-soluble bars it has already been suggested to mix the various constituents and then pour the mixture obtained, while hot, into a mould. After cooling, the mixture crystallizes so as to yield a bar of water-soluble material which may then be positioned in a perforated container adapted to be suspended in a toilet bowl. This method of manufacture has the disadvantage that it is relatively expensive. In order to reduce the cost of manufacture it has also been suggested in French Pat. No. 2,020,577 that the various liquid and powdered components entering into the water-soluble products by mixed and that the mixture then be extruded while cold through an extrusion nozzle. However, it has been found by applicants that it is practically impossible to prepare hydrosoluble bars having a conventional composition using this technique because of difficulties which arise in adjusting the consistency of the mixture to be extruded. In effect, the mixture to be extruded is either too hard so that it lacks plasticity and may block the extrusion nozzle, or too liquid in which case it cannot be extruded. Moreover, the extruded products have properties which are poorer than those which are produced in the hot pouring process. They lack cohesion and have a tendency to disintegrate in the course of use which leads to an excessively rapid erosion of the product.

It is the object of the present invention to overcome these disadvantages and for that reason it is proposed to provide a block of hydrosoluble material obtained by extrusion having characteristics during use comparable to those of hydrosoluble products prepared by hot moulding.

It is therefore an object of the present invention to provide a composition adapted for the manufacture of a hydrosoluble product having a solid form by extrusion at room temperature, in particular in the form of a bar adapted to dissolve in the flushing water of a toilet bowl, said composition containing paradichlorobenzene and being characterized by the fact that it contains a water-soluble extrusion additive which acts as a binder and is malleable at room temperature, said additive having a softening point below 45° C. and being capable of subliming before reaching its melting point at a temperature greater than 52° C.

In a preferred embodiment of the composition according to the invention, the extrusion additive is a foaming agent under the conditions of use of the hydrosoluble product prepared from the composition. The extrusion additive is a paraffin sulfonate consisting of sulfonated alkyl chains having 14 to 16 carbon atoms and having a high monosulfonate content. The paraffin sulfonate serving as an extrusion additive contains about 95% monosulfonate and about 5% polysulfonates. The composition contains at least one anionic detergent, at least one fatty amide, and preferably a monoethanolamide of a fatty acid. The composition also contains mineral salts and preferably sodium sulfates. Preferably, the composition contains 10 to 40% of paradichlorobenzene, from 5 to 30% of anionic detergent, from 1 to 10% of monoethanolamide of fatty acid, from 10 to 50% of anhydrous sodium sulfate, 5 to 30% of paraffin sulfonate, and 1 to 5% perfume, the percentages being given by weight as a percentage of the total composition.

It has been found that the mixture of the various constituents entering into the composition according to the invention may be easily extruded after its introduction into an extruding device by reason of the presence of the extrusion additive which imparts to the mixture the plasticity and consistency required for this type of operation. The extrusion additive which is incorporated into the composition has a softening point below 45° C. so as to prevent any release of the paradichlorobenzene contained in the mixture during the extrusion.

It also has the property of subliming before reaching its melting point at a temperature above 52° C., this temperature of 52° C. being substantially the melting point of paradichlorobenzene.

The extrusion additive is readily soluble in water during the use of the bar of hydrosoluble product obtained by extruding the mixture, and has, preferably, a foaming rather than an anti-foaming property.

The extrusion additive which has been described and which is incorporated into the composition for toilet bowls is, preferably, a paraffin sulfonate consisting of alkyl chains having from 14 to 16 carbon atoms and a high percentage of monosulfonate. Such a product is available under the name "WAROLAT U" sold commercially by the Bayer Company. It is in the form of flakes which are soluble in water and contain 93-95% by weight of the active substance in its commercial foam. About 95% of this is monosulfonate and 5% diand polysulfonate.

The composition according to the invention contains anionic detergents having a foaming effect. Alkaline salts, and in particular sodium salts, are preferably used. Good results are obtained with sodium laurylsulfate and sodium oleylmethyltauride.

The composition according to the invention also contains fatty amides in admixture with the paradichlorobenzene and the extrusion additive. The fatty amides utilized are advantageously monoethanolamides of fatty acids such as copra monoethanolamide or lauric monoethanolamide for example. They have the property of exerting a synergistic effect on the foaming of the anionic detergents contained in the product during use of the bar and simultaneously stabilizing this foam. Finally, they make it possible to adjust the speed of erosion of the hydrosoluble bar in the course of use. It has been noted that the length of use before complete exhaustion of the bar of hydrosoluble product is dependent on the percentage of fatty amides in the composition.

The mineral salts of the sodium sulfate type incorporated in the composition have the property of assuring the retention in bar form of the constituents included in the hydrosoluble bar when it is in contact with the water. This characteristic is particularly valuable since it permits improvement of the cohesion and thus an increase in the useful life of a hydrosoluble bar.

Other agents known in the state of the art may also be incorporated in the composition according to the invention. These include perfumes, solid detergents, colorants, inert materials such as talc, and sequestering agents. The colorants which are included in this mixture are preferably of a pigmentary nature so as to avoid the formation of lines of colorant on the wall of the toilet bowl during the course of use of the hydrosoluble bar.

It is also an object of the present invention to manufacture by extrusion a hydrosoluble product in the form of a solid, and in particular in the form of a bar, having the above defined composition. This bar is characterized by the fact that the constituents entering into the composition of the hydrosoluble product are mixed, the mixture obtained is milled at room temperature, followed by extrusion at a temperature between 10° and 40° C., the final product being then cut to the length desired. The milling operation which is carried out, for example, on a mill having smooth rolls, makes it possible to obtain flakes or sheets of product which have the consistency and homogeneity necessary for extrusion. Once this step has been carried out, the flakes are introduced into an extruder of the usual type so as to produce extrusions which are cut and and treated in view of their intended use. It should be noted that the cohesion of the mixture is assured during the milling and extrusion step by the presence of an extrusion additive. The bars of hydrosoluble product prepared in accordance with the process of the invention have characteristics which are comparable to those of hydrosoluble products made in accordance with the prior art by hot moulding and with respect to their useful life and cohesion are capable of progressively dissolving without disintegrating in the flushing water of toilet bowls during their use.

Finally, the present invention has as its object the new article of manufacture which consists of a solid hydrosoluble product, particularly in the form of a bar, preferably prepared in accordance with the above process and characterized by the fact that it contains 10 to 40% paradichlorobenzene, from 5 to 30% of anionic detergent, 1 to 10% of monoethanolamide of fatty acids, from 10 to 50% of anhydrous sodium sulfate, from 5 to 30% of paraffin sulfate, and 1 to 5% perfume, the percentages being given by weight of the total product.

In order that the object of the invention may be better understood, several embodiments thereof will now be described purely by way of illustration and example.

In order to manufacture hydrosoluble bars by extrusion, a homogeneous mixture of the various constituents in the proportions by weight specified above, is prepared in the following examples. These constituents are in the form of powders, solids and liquids. The extrusion additive used in these examples is paraffin sulfonate commercially sold as WAROLAT U by the Bayer Chemical Company. The mixture is prepared and the paste milled at room temperature in a mill having smooth rolls. This produces smooth flakes or sheets which are then introduced into an extruder, the chamber of which is maintained at 15° C. The extrusions obtained at the outlet of the extruder are divided into sections and introduced into cages adapted to be suspended from the edge of a toilet bowl.

EXAMPLE 1

| | | |
|---|---|---|
| Paradichlorobenzene | 10 | % |
| Sodium sulfate | 50 | % |
| Sodium oleylmethyltauride | 13 | % |
| Monoethanolamide of fatty acid of copra | 10 | % |
| Perfume | 1 | % |
| Paraffin sulfonate | 15.99 | % |
| Pigmentary dye | 0.01 | % |
| | 100.0 | % |

EXAMPLE 2

| | | |
|---|---|---|
| Paradichlorobenzene | 40 | % |
| Sodium sulfate | 10 | % |
| Sodium laurylsulfate | 30 | % |
| Lauric monoethanolamide | 1 | % |
| Perfume | 5 | % |
| Paraffin sulfonate | 5 | % |
| Talc | 8.95 | % |
| Pigmentary dye | 0.05 | % |
| | 100.0 | % |

EXAMPLE 3

| | | |
|---|---|---|
| Paradichlorobenzene | 12.99 | % |
| Sodium sulfate | 50 | % |
| Sodium oleylmethylauride | 5 | % |
| Monoethanolamide of copra | 1 | % |
| Perfume | 1 | % |
| Paraffin sulfonate | 30 | % |
| Pigmentary dye | 0.01 | % |
| | 100.0 | % |

EXAMPLE 4

| | | |
|---|---|---|
| Paradichlorobenzene | 29.99 | % |
| Sodium sulfate | 26 | % |
| Monoethanolamide of copra | 2 | % |
| Sodium laurylsulfate | 17 | % |
| Paraffin sulfonate | 12 | % |
| Perfume | 2 | % |
| Talc | 11 | % |
| Pigmentary dye | 0.01 | % |
| | 100.0 | % |

EXAMPLE 5

| | | |
|---|---|---|
| Paradichlorobenzene | 29.99 | % |
| Sodium sulfate | 31 | % |
| Monoethanolamide of fatty acid of copra | 2 | % |
| Sodium laurylsulfate | 20 | % |
| Paraffin sulfonate | 15 | % |
| Perfume | 2 | % |
| Pigmentary dye | 0.01 | % |
| | 100.0 | % |

EXAMPLE 6

| | | |
|---|---|---|
| Paradichlorobenzene | 30 | % |
| Sodium sulfate | 26 | % |
| Monoethanolamide of fatty acid of copra | 2 | % |
| Sodium laurylsulfate | 20 | % |
| Paraffin sulfonate | 15 | % |
| Perfume | 2 | % |
| Disodic salt of tetracetic ethylene diamime | 5 | % |

| | |
|---|---|
| | 100 % |

It has been found that hydrosoluble bars having the compositions of Examples 1 to 6 have excellent cohesion during use. They dissolve gradually without disintegrating in the flushing water and, since they have an adequate paradichlorobenzene content, they are quite efficacious. It will, of course, be appreciated that the embodiments which have just been described have been given purely by way of illustration and example, and may be modified as to detail without thereby departing from the basic principles of the invention.

What is claimed is:

1. Composition for extruding a hydrosoluble toilet bowl bar which is solid at room temperature and adapted to dissolve in the flushing water of a toilet bowl, said composition comprising 10-40% by weight of paradichlorobenzene, 5-30% by weight of a paraffin sulfonate which improves the cohesion and consistency of the composition and is constituted by sulfonated alkyl chains having 14-16 carbon atoms 5-30% of a foamable anionic detergent other than a paraffin sulfonate, and at least 1-10% of at least one fatty amide which controls the speed of errosion of said bar.

2. Composition as claimed in claim 1 in which the paraffin sulfonate contains about 95% monosulfonate and 5% polysulfonates.

3. Composition as claimed in claim 1 which also contains 10-50% mineral salts which improve the cohesion of said bar and 1-5% perfume.

4. Composition as claimed in claim 3 in which said amide is a monoethanolamide of a fatty acid.

5. Composition as claimed in claim 3 in which said mineral salt is sodium sulfate.

6. Hydrosoluble composition as claimed in claim 1 in the form of an extruded bar.

7. Process of manufacturing a hydrosoluble product as claimed in claim 1 by extrusion in solid form, which process comprises the steps of mixing the constituents of said composition, rolling the resulting mixture at ambient temperature, extruding said mixture at a temperature between 10° and 40° C., and cutting the final product to the length desired.

* * * * *